United States Patent
Ye et al.

(10) Patent No.: US 12,334,215 B2
(45) Date of Patent: Jun. 17, 2025

(54) METHOD FOR IDENTIFYING ANESTHETIC DRUG, AND METHOD AND DEVICE FOR PROCESSING ANESTHESIA ELECTROENCEPHALOGRAM SIGNAL

(71) Applicant: SHENZHEN MINDRAY BIO-MEDICAL ELECTRONICS CO., LTD., Shenzhen (CN)

(72) Inventors: Zhigang Ye, Shenzhen (CN); Xingliang Jin, Shenzhen (CN); Xianliang He, Shenzhen (CN); Ningling Zhang, Shenzhen (CN); Hanyuan Luo, Shenzhen (CN); Ming Li, Shenzhen (CN); Zuming Yao, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 1389 days.

(21) Appl. No.: 16/914,648

(22) Filed: Jun. 29, 2020

(65) Prior Publication Data
US 2020/0327995 A1     Oct. 15, 2020

Related U.S. Application Data

(63) Continuation of application No. PCT/CN2017/120348, filed on Dec. 29, 2017.

(51) Int. Cl.
*G06F 11/30*      (2006.01)
*A61B 5/00*       (2006.01)
(Continued)

(52) U.S. Cl.
CPC ......... *G16H 40/63* (2018.01); *A61B 5/4821* (2013.01); *G16H 50/20* (2018.01); *G16H 70/40* (2018.01); *G06F 2218/08* (2023.01)

(58) Field of Classification Search
CPC .................................................... G16H 40/63
See application file for complete search history.

(56) References Cited

U.S. PATENT DOCUMENTS

2002/0173729 A1   11/2002   Viertio-Oja et al.
2003/0055355 A1    3/2003   Viertio-Oja
(Continued)

FOREIGN PATENT DOCUMENTS

CN     101301196 A      11/2008
CN     101366033 A       2/2009
(Continued)

OTHER PUBLICATIONS

First Office Action issued in related Chinese Application No. 201780085019.2, mailed Apr. 26, 2021, 11 pages.
(Continued)

*Primary Examiner* — Phuong Huynh
(74) *Attorney, Agent, or Firm* — BAYES PLLC

(57) ABSTRACT

A method for processing an anesthesia electroencephalogram signal is disclosed. The method includes acquiring an electroencephalogram signal by means of an electroencephalogram sensor; selecting a target anesthesia depth model from an anesthesia depth model database according to the type of a drug for anesthesia, each anesthesia depth model of the anesthesia depth model database being trained according to a specific drug type, a corresponding electroencephalogram signal, and a marked anesthesia depth; and obtaining an anesthesia depth value on the basis of the target anesthesia depth model and the electroencephalogram signal. In the processing method, according to the type of an anesthetic drug, an appropriate anesthesia depth model is selected, so that the depth of anesthesia can be obtained more accurately, and the adaptability to the type of the anesthetic drug is increased.

15 Claims, 6 Drawing Sheets

(51) Int. Cl.
  *G16H 40/63* (2018.01)
  *G16H 50/20* (2018.01)
  *G16H 70/40* (2018.01)

(56) References Cited

U.S. PATENT DOCUMENTS

2013/0331660 A1  12/2013  Al-Ali et al.
2014/0316217 A1  10/2014  Purdon et al.

FOREIGN PATENT DOCUMENTS

| | | | |
|---|---|---|---|
| CN | 102355913 A | | 2/2012 |
| CN | 102564521 A | | 7/2012 |
| CN | 103432651 | * | 12/2012 |
| CN | 103153178 A | | 6/2013 |
| CN | 103432651 A | | 12/2013 |
| CN | 103735261 A | | 4/2014 |
| CN | 104869897 A | | 8/2015 |
| CN | 105925727 A | * | 9/2016 |
| CN | 106955403 | * | 7/2017 |
| CN | 116369948 A | * | 7/2023 |
| EP | 2535000 A1 | * | 12/2012 ........... A61B 5/0205 |

OTHER PUBLICATIONS

International Search Report issued in corresponding International Application No. PCT/CN2017/120348, mailed Sep. 19, 2018, 5 pages.

* cited by examiner

| Drug setting area | | | | | Anesthesia depth setting area | |
|---|---|---|---|---|---|---|
| Drug Target | Drug result | Operation area | | | Anesthesia depth target | Anesthesia depth value |
| Propofol | Propofol | Confirm | Edit | Cancel | | |
| Sevoflurane | Sevoflurane | Confirm | Edit | Cancel | | |
| Ketamine | Ketamine | Confirm | Edit | Cancel | 47 | 50 |
| Dexmedetomidine | Dexmedetomidine | Confirm | Edit | Cancel | | |
| ...... | ...... | Confirm | Edit | Cancel | | |

METHOD FOR IDENTIFYING ANESTHETIC DRUG, AND METHOD AND DEVICE FOR PROCESSING ANESTHESIA ELECTROENCEPHALOGRAM SIGNAL

CROSS-REFERENCE TO RELATED APPLICATION

This application is a continuation of PCT Application No. PCT/CN2017/120348, filed Dec. 29, 2017, entitled "METHOD FOR IDENTIFYING ANESTHETIC DRUG, AND METHOD AND DEVICE FOR PROCESSING ANESTHESIA ELECTROENCEPHALOGRAPHY SIGNAL," the entire contents of which are incorporated herein by reference.

TECHNICAL FIELD

The present disclosure relates to the field of induced electrophysiological signal processing, and in particular to a method for identifying an anesthetic drug, and a method and device for processing an anesthesia electroencephalogram signal.

BACKGROUND

Anesthesia refers to the use of a drug or other methods to make a patient in whole or in part lose the sensation temporarily to achieve the purpose of painlessness for surgical treatment. The anesthesia process requires continuous, real-time and non-invasive display of changes in the anesthesia depth, which can finely reflect changes in the concentration of the anesthetic drug. If the anesthesia is too deep or too shallow, it will cause harm to the patient. Excessive use of the anesthetic drug or the anesthesia is too deep may cause increased postoperative complications of the patient. Insufficient use of the anesthetic drug or the anesthesia is too shallow may cause the patient to suffer from intraoperative awareness, which may cause the patient to suffer from postoperative physical and mental disability, and bring great medical and legal responsibilities to doctors.

In the prior art, a means for assessing the level of consciousness of the patient during general anesthesia is to use OAAS scale (sedation scale). There are a total of six levels for OAAS. The determination and clinical grading of each level are shown in Table 1:

TABLE 1

OAAS scale

| Score | Determination | Degree of anesthesia |
|---|---|---|
| 5 | Normal response to name called normally | Alertness |
| 4 | Sluggish response to name called normally | |
| 3 | Respond to name called loudly or repeatedly | |
| 2 | Respond to tapping or shaking | Anesthesia |
| 1 | Respond to noxious stimulus | |
| 0 | Do not respond to noxious stimulus | |

In actual clinical applications, the subjective scoring of clinical grading is relatively cumbersome to perform, which will bring more burdens to medical personnel, and cannot be operated continuously.

Electroencephalogramelectroencephalogramelectroencephalogramelectroencephalogramelectroencephalogram

SUMMARY

A first aspect of the present disclosure provides a method for identifying an anesthetic drug. The method comprises: acquiring an electroencephalogram signal by means of an electroencephalogram sensor; de-noising the electroencephalogram signal; extracting a signal characteristic of the de-noised electroencephalogram signal; and determining the drug type according to the signal characteristic and a preset prediction model, and the prediction model comprising a correspondence relationship between at least one signal characteristic of an electroencephalogram signal and a type of drug.

In the present disclosure, the prediction model comprises the correspondence relationship between an electroencephalogram signal and the prediction model. The signal characteristic and the preset prediction model are used to determine the drug type. In this case, the prediction model can be automatically confirmed on the basis of the collected electroencephalogram signal.

The method for identifying an anesthetic drug according to the first aspect of the present disclosure further comprises displaying the drug type. As a result, the drug type can be obtained intuitively.

In the method for identifying an anesthetic drug according to the first aspect of the present disclosure, the signal characteristic comprises one or more of a time-domain characteristic, a frequency-domain characteristic, and a non-linear-domain characteristic. As a result, the drug type can be confirmed on the basis of one or more of the signal characteristics and the prediction model.

In the method for identifying an anesthetic drug according to the first aspect of the present disclosure, the time-domain characteristic comprises an amplitude characteristic of the electroencephalogram signal, the frequency-domain characteristic comprises an electroencephalogram-related energy ratio, and the nonlinear-domain characteristic comprises an LZ complexity, a spectral entropy, a sample entropy, or an information entropy. As a result, the drug type can be confirmed on the basis of one or more of the amplitude characteristic, the electroencephalogram-related energy ratio, the LZ complexity, the spectral entropy, the sample entropy or the information entropy of the electroencephalogram signal, and the prediction model.

In the method for identifying an anesthetic drug according to the first aspect of the present disclosure, the prediction model is trained with specific types of drugs and corresponding electroencephalogram signals. As a result, after the prediction model receives the collected electroencephalogram signal, the drug type can be obtained.

In the method for identifying an anesthetic drug according to the first aspect of the present disclosure, the drug type database further comprises population information, drug information and the type of surgery, which correspond to the electroencephalogram signal throughout the anesthesia. As a result, there are many types of data recorded in the database with types of drugs, such that the trained prediction model has a wide coverage.

A second aspect of the present disclosure provides a method for processing an anesthesia electroencephalogram signal. The method comprises: acquiring an electroencephalogram signal by means of an electroencephalogram sensor; selecting a target anesthesia depth model from an anesthesia depth model database according to the type of a drug for anesthesia, the anesthesia depth model database being trained according to a specific drug type, a corresponding electroencephalogram signal, and a marked anesthesia depth; and obtaining an anesthesia depth value on the basis of the target anesthesia depth model and the electroencephalogram signal.

In the present disclosure, each drug type has a corresponding anesthesia depth model, the target anesthesia depth model is selected according to the type of the anesthetic drug, and the anesthesia depth value is obtained on the basis of the target anesthesia depth model and the electroencephalogram signal. In this case, the anesthesia depth can be obtained more accurately, and the adaptability to the type of the anesthetic drug is increased.

In the method for processing an anesthesia electroencephalogram signal according to the second aspect of the present disclosure, before the step of obtaining the anesthesia depth value based on the target anesthesia depth model and the electroencephalogram signal, the method further comprises: displaying the drug type. As a result, the drug type can be obtained while obtaining the anesthesia depth value.

The method for processing an anesthesia electroencephalogram signal according to the second aspect of the present disclosure further comprises outputting the anesthesia depth value. As a result, the anesthesia depth value can be obtained intuitively.

In the method for processing an anesthesia electroencephalogram signal according to the second aspect of the present disclosure, the step of obtaining the anesthesia depth value based on the target anesthesia depth model and the electroencephalogram signal further comprises: extracting a signal characteristic of the de-noised effective electroencephalogram signal; and obtaining the anesthesia depth value based on the target anesthesia depth model and the signal characteristic. As a result, the anesthesia depth can be obtained more accurately.

In the method for processing an anesthesia electroencephalogram signal according to the second aspect of the present disclosure, the signal characteristic comprises one or more of a time-domain characteristic, a frequency-domain characteristic, and a nonlinear-domain characteristic. As a result, the anesthesia depth corresponding to the electroencephalogram signal can be obtained from the characteristics of various aspects.

In the method for processing an anesthesia electroencephalogram signal according to the second aspect of the present disclosure, the drug type is automatically identified according to the signal characteristic of the electroencephalogram signal and a preset prediction model comprising a correspondence relationship between signal characteristics of electroencephalogram signals and types of drugs. As a result, the work efficiency of health care personnel can be improved.

In the method for processing an anesthesia electroencephalogram signal according to the second aspect of the present disclosure, the drug type is inputted by a user. As a result, the accuracy of the prediction model can be ensured.

In the method for processing an anesthesia electroencephalogram signal according to the second aspect of the present disclosure, the drug type is automatically identified according to the signal characteristic of the electroencephalogram signal and a preset prediction model, and confirmed by user input, the prediction model comprising a correspondence relationship between at least one signal characteristic of an electroencephalogram signal and a drug type. As a result, the work efficiency of the health care personnel can be improved while ensuring the accuracy of the prediction model.

A third aspect of the present disclosure provides a device for processing an anesthesia electroencephalogram signal. The device comprises: a collection module for acquiring an electroencephalogram signal by means of an electroencephalogram sensor; and an anesthesia depth computing module for selecting a target anesthesia depth model from an anesthesia depth model database according to the type of a drug for anesthesia, the anesthesia depth model database being trained according to a specific type of drug, a corresponding electroencephalogram signal, and a marked anesthesia depth; and for obtaining an anesthesia depth value on the basis of the target anesthesia depth model and the electroencephalogram signal.

In the present disclosure, the anesthesia depth model database includes an anesthesia depth model corresponding to each type of drug. The target anesthesia depth model is selected according to the type of the anesthetic drug, and the anesthesia depth value is obtained based on the target anesthesia depth model and the electroencephalogram signal. In this case, the anesthesia depth can be obtained more accurately, and the adaptability to the type of the anesthetic drug is increased.

The device for processing an anesthesia electroencephalogram signal according to the third aspect of the present disclosure further comprises a display module for displaying the drug type and the anesthesia depth value; and/or a de-noising module for de-noising the acquired electroencephalogram signal. As a result, the drug type and the anesthesia depth value can be obtained intuitively, and the signal quality of the electroencephalogram signal can be improved.

A fourth aspect of the present disclosure provides a device for processing an anesthesia electroencephalogram signal. The device comprises: a sensor for collecting an electroencephalogram signal; a memory for storing the collected electroencephalogram signal; and a processor for performing the following steps: extracting a signal characteristic of the electroencephalogram signal; and determining the drug type according to the signal characteristic and a preset prediction model comprising a correspondence relationship between signal characteristics of electroencephalogram signals and types of drugs. In this case, the prediction model can be automatically confirmed based on the collected electroencephalogram signal.

In the device for processing an anesthesia electroencephalogram signal according to the fourth aspect of the present disclosure, before performing the steps, the processor further performs de-noising on the acquired electroencephalogram signal. As a result, the signal quality of the electroencephalogram signal can be improved. The drug type can be confirmed more accurately.

In the device for processing an anesthesia electroencephalogram signal according to the fourth aspect of the present disclosure, the signal characteristic comprises one or more of a time-domain characteristic, a frequency-domain characteristic, and a nonlinear-domain characteristic. As a result, the drug type can be confirmed based on one or more of the signal characteristics and the prediction model.

In the device for processing an anesthesia electroencephalogram signal according to the fourth aspect of the present disclosure, the processor is further used to perform the following steps: selecting a target anesthesia depth model from an anesthesia depth model database according to the determined drug type, the anesthesia depth model database being trained according to a specific drug type, a corresponding electroencephalogram signal, and a marked anesthesia depth; and obtaining an anesthesia depth value based on the target anesthesia depth model and the electroencephalogram signal. In this case, the anesthesia depth can be obtained more accurately, and the adaptability to the type of the anesthetic drug is increased.

In the device for processing an anesthesia electroencephalogram signal according to the fourth aspect of the present disclosure, the step of obtaining the anesthesia depth value based on the target anesthesia depth model and the electroencephalogram signal comprises: extracting a signal characteristic of the electroencephalogram signal; and obtaining the anesthesia depth value based on the target anesthesia depth model and the signal characteristic. As a result, the anesthesia depth can be obtained more accurately.

DETAILED DESCRIPTION OF EMBODIMENTS

Figure 1:
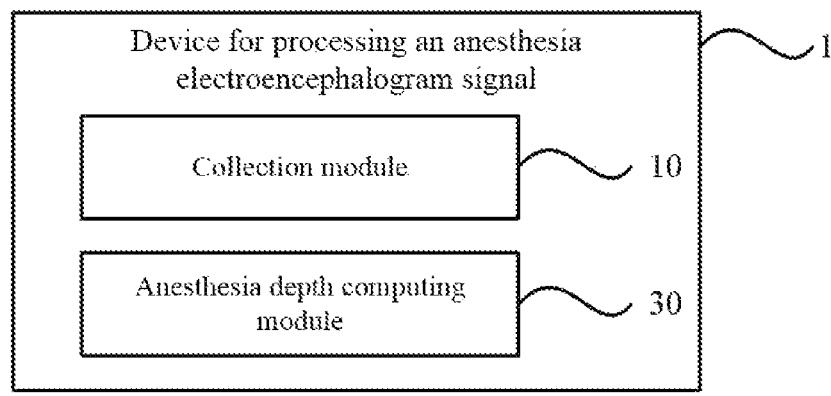
FIG. 1 is a schematic diagram showing modules of a device for processing an anesthesia electroencephalogram signal according to an embodiment of the present disclosure.

Preferred embodiments of the present disclosure are described below in detail with reference to the accompanying drawings. In the following description, the same components are provided with the same reference numerals. Repeated description is omitted. In addition, the accompanying drawings are schematic figures. The proportions among the sizes of the components, the shapes of the components, and the like may be different from those in reality.

Figure 2:
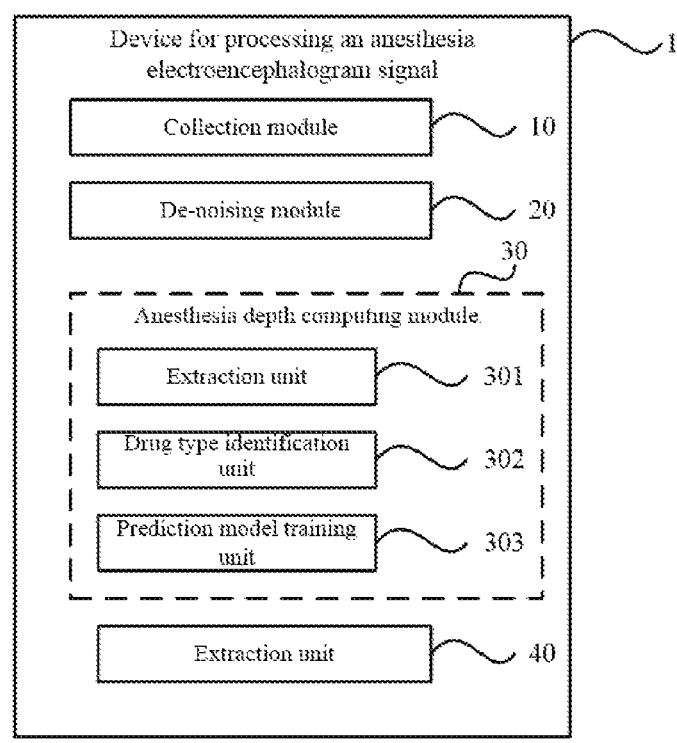
FIG. 2 is a schematic diagram showing modules of another device for processing an anesthesia electroencephalogram signal according to an embodiment of the present disclosure.

FIG. 1 is a schematic diagram showing modules of a device for processing an anesthesia electroencephalogram signal according to an embodiment. FIG. 2 is a schematic diagram showing modules of another device for processing an anesthesia electroencephalogram signal according to an embodiment.

In this embodiment, as shown in FIG. 1, a device 1 for processing an anesthesia electroencephalogram signal may comprise a collection module 10 and an anesthesia depth computing module 30.

In this embodiment, the collection module 10 may be used to acquire an electroencephalogram signal by means of an electroencephalogram sensor. In some examples, the collection module 10 may be a sensor. For example, the collection of the electroencephalogram signal may be obtained by means of electrode pads. In addition, the collection module 10 may also be other EEG collection apparatuses. The collected electroencephalogram signal may comprise various segments of the electroencephalogram signal throughout the anesthesia of the patient.

In this embodiment, the device 1 for processing an anesthesia electroencephalogram signal may further comprise an analog-to-digital conversion module (not shown). The analog-to-digital conversion module can perform analog-to-digital conversion on the collected analog electroencephalogram signal. That is, the analog-to-digital conversion module can convert the analog electroencephalogram signal into a digital electroencephalogram signal. As a result, this facilitates the storage of the electroencephalogram signal.

In this embodiment, the electroencephalogram signal collected by the collection module 10 generally comprises interference signals, which affect the signal quality of the electroencephalogram signal. As shown in FIG. 2, a device 1 for processing an anesthesia electroencephalogram signal may further comprise a de-noising module 20. The de-noising module 20 is used to de-noise the acquired electroencephalogram signal. De-noising may comprise filtering low-frequency interference through high-pass filtering, filtering high-frequency interference through low-pass filtering, and detecting and removing interference signals such as electrooculograms and electromyograms.

In some embodiments, the de-noising module 20 may comprise a high-pass filtering device, such as a high-pass filter. The high-pass filtering device can filter out low-frequency interference. The de-noising module 20 may further comprise a low-frequency filtering device, such as a low-pass filter. The low-pass filtering device can filter out high-frequency interference. The de-noising module 20 may also detect and remove the interference signals such as electrooculograms and electromyograms. However, this embodiment is not limited thereto, and the de-noising module 20 may also be a processor with a de-noising function.

In addition, in this embodiment, the device 1 for processing an anesthesia electroencephalogram signal may further comprise a memory (not shown). The memory can be used to store the collected electroencephalogram signal. In some embodiments, the memory is connected to the collection module 10, in which case, the electroencephalogram signal collected by the collection module 10 may be stored in the memory.

In this embodiment, as shown in FIG. 2, the device 1 for processing an anesthesia electroencephalogram signal may further comprise an anesthesia depth computing module 30.

The anesthesia depth computing module 30 may be a processor. For example, it is a central processing unit (CPU), a microprocessor unit (MPU), an application specific integrated circuit (ASIC), etc.

In this embodiment, the electroencephalogram signal has a signal characteristic. The anesthesia depth computing module 30 may comprise an extraction unit 301. The extraction unit 301 is used to extract the signal characteristic of the de-noised electroencephalogram signal. The signal characteristic may comprise at least one of a time-domain characteristic, a frequency-domain characteristic, and a nonlinear-domain characteristic. The time-domain characteristic comprises an amplitude characteristic of the electroencephalogram signal, the frequency-domain characteristic comprises an electroencephalogram-related energy ratio, and the nonlinear-domain characteristic comprises an LZ complexity, a spectral entropy, a sample entropy, or an information entropy.

In this embodiment, the signal characteristic may be extracted per time period. That is, the signal characteristic can be extracted periodically. The time period of extraction may be a fixed value. That is, the period of extraction remains unchanged. However, this embodiment is not limited thereto, and the time period of extraction may also be a variable value. That is, the period of extraction will change according to the actual situation.

In this embodiment, the anesthesia depth computing module 30 further comprises a drug identification unit 302 for selecting a target anesthesia depth model from an anesthesia depth model database according to the type of a drug for anesthesia. Each anesthesia depth model of the anesthesia depth model database being trained according to a specific drug type, a corresponding electroencephalogram signal, and a marked anesthesia depth. The anesthesia depth computing module obtains an anesthesia depth value based on the target anesthesia depth model and the electroencephalogram signal.

In this embodiment, the anesthesia depth model database may comprise a plurality of anesthesia depth models. Each anesthetic drug corresponds to one of the anesthesia depth models. Each anesthesia depth model is trained with a corresponding specific anesthesia depth database.

In this embodiment, the specific anesthesia depth database for each drug includes electroencephalogram signals of people of different ages and from different populations under the specific drug, corresponding anesthesia depths recorded by doctors based on these electroencephalogram signals, and a correspondence relationship between various segments of the electroencephalogram signal and anesthesia depths (that is, a correspondence relationship between signal characteristics of various segments of the electroencephalogram signal and anesthesia depths). Anesthetic states corresponding to various segments of the electroencephalogram signal comprise one or more of alertness, sedation, normal anesthesia, deep anesthesia, excessive deep anesthesia, and no electrical brain activity.

In this embodiment, the anesthesia depth model for each drug may be trained with the corresponding specific anesthesia depth database. Specifically, the anesthesia depth model for each anesthetic drug may be trained by the anesthesia depth computing module 30 with the signal characteristic of the electroencephalogram signal and the anesthetic states corresponding to various segments of the electroencephalogram signal in the specific anesthesia depth database.

In this embodiment, according to the drug type for anesthesia, the anesthesia depth computing module 30 may select a target anesthesia depth model from the anesthesia depth model database, and obtain an anesthesia depth value according to the signal characteristic of the collected electroencephalogram signal and the target anesthesia depth model. In some examples, the electroencephalogram signals collected by the collection module 10 are processed by the de-noising module 20. As a result, the anesthesia depth computing module 30 may also obtain the anesthesia depth value based on the target anesthesia depth model and the signal characteristic of the de-noised electroencephalogram signal. As a result, the anesthesia depth can be obtained more accurately.

In this embodiment, the drug type used by the anesthesia depth computing module 30 may be input by a user. That is, the health care personnel can manually select the drug type and select a target anesthesia depth model from the anesthesia depth model database of the anesthesia depth computing module 30 according to the type of the anesthetic drug used. As a result, the accuracy of the prediction model can be ensured.

However, this embodiment is not limited thereto, and the drug type used by the anesthesia depth computing module 30 may also be automatically identified. That is, it is also possible that the device 1 for processing an anesthesia electroencephalogram signal automatically identifies the drug type, and then automatically selects a target anesthesia depth model from the anesthesia depth model database of the anesthesia depth computing module 30. As a result, the work efficiency of health care personnel can be improved.

However, this embodiment is not limited thereto, and the drug type used by the anesthesia depth computing module 30 may also be automatically identified by the device, and confirmed by user input. As a result, the work efficiency of the health care personnel can be improved while ensuring the accuracy of the prediction model.

In this embodiment, the anesthesia depth computing module 30 needs a drug type identification unit 302 to complete the automatic drug identification function.

In this embodiment, as shown in FIG. 2, the anesthesia depth computing module 30 may further comprise a drug type identification unit 302. The drug type identification unit 302 is used to confirm the drug type according to the signal characteristic of the electroencephalogram signal collected by the electroencephalogram sensor and the preset prediction model comprising the correspondence relationship between the signal characteristics of electroencephalogram signals and the types of drugs. As a result, the drug type can be automatically identified. The signal characteristic on which the drug type identification unit 302 is based is collected by the extraction unit 301. In addition, the electroencephalogram signal used for the extraction of the signal characteristic may also be the electroencephalogram signal processed by the de-noising module 20.

In this embodiment, as shown in FIG. 2, the anesthesia depth computing module 30 may further comprise a prediction model training unit 303. The prediction model training unit 303 is used to train a prediction model according to the specific drug type and the corresponding electroencephalogram signal.

Figures 3A, 3B, 3C, 3D, 4:
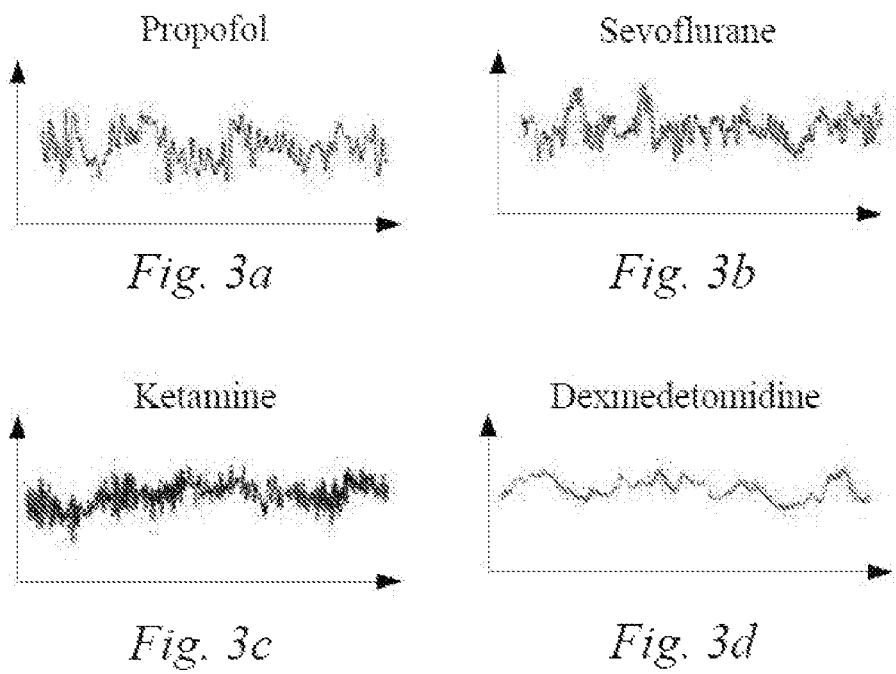
FIG. 3a is a schematic diagram showing a time-domain waveform under the action of an anesthetic drug propofol according to an embodiment of the present disclosure.
FIG. 3b is a schematic diagram showing a time-domain waveform under the action of an anesthetic drug sevoflurane according to an embodiment of the present disclosure.
FIG. 3c is a schematic diagram showing a time-domain waveform under the action of an anesthetic drug ketamine according to an embodiment of the present disclosure.
FIG. 3d is a schematic diagram showing a time-domain waveform under the action of an anesthetic drug dexmedetomidine according to an embodiment of the present disclosure.
FIG. 4 is a schematic diagram showing an interface of a display module according to an embodiment of the present disclosure.

FIG. 3a is a schematic diagram showing a time-domain waveform under the action of an anesthetic drug propofol according to an embodiment. FIG. 3b is a schematic diagram showing a time-domain waveform under the action of an anesthetic drug sevoflurane according to an embodiment. FIG. 3c is a schematic diagram showing a time-domain waveform under the action of an anesthetic drug ketamine according to an embodiment. FIG. 3d is a schematic diagram showing a time-domain waveform under the action of an anesthetic drug dexmedetomidine according to an embodiment.

In this embodiment, different drugs act on the central nervous system, such that the produced electroencephalogram signals are different. As shown in FIGS. 3a to 3d, for anesthetic drugs such as propofol, sevoflurane, ketamine and dexmedetomidine, these different types of anesthetic drugs act on the central nervous system, such that the produced electroencephalogram signals are different. As a result, there is a correspondence relationship between the types of drugs and the corresponding electroencephalogram signals. A prediction model can be trained by using the recorded a specific drug type, the corresponding electroencephalogram signal, and the correspondence relationship between the electroencephalogram signal and the drug type.

In this embodiment, the prediction model is trained with a marked drug type database. In other words, the types of the drugs and the electroencephalogram signals for training the prediction model are stored in the drug type database. The electroencephalogram signals in the drug type database are electroencephalogram signals of patients at an anesthetic state that are recorded by the health care personnel. The drug database further comprises various types of drugs, and the correspondence relationship between the types of drugs and corresponding electroencephalogram signals. Specifically, the drug type database further comprises a correspondence relationship between the types of drugs and the signal characteristics of the corresponding electroencephalogram signals. The signal characteristic comprises at least a frequency-domain characteristic of the electroencephalogram signal. However, this embodiment is not limited thereto, and the signal characteristic may also comprise at least one of a time-domain characteristic and a nonlinear-domain characteristic.

In this embodiment, the drug type database includes electroencephalogram signals of people of different ages and from different populations under specific types of drugs. The prediction model is trained with the drug type database. That is, the prediction model is trained with the specific drug type and the corresponding electroencephalogram signals.

In this embodiment, the drug type database further comprises population information, drug information and the type of surgery, which correspond to the electroencephalogram signal throughout the anesthesia. The population information may be population coverage. The population coverage may refer to coverage for all ages, divided into children (0 to 13 years old], adults (13 to 60 years old], and elderly people (over 60 years old).

In this embodiment, the drug information may be drug coverage. The drug coverage mainly refers to the collection of anesthesia data of sedative, analgesic and muscle relaxant drugs used for mainstream intravenous and gas anesthesia, including but not limited to the following types: propofol, etomidate, midazolam, dexmedetomidine, isoflurane, sevoflurane, desflurane, fentanyl, remifentanil, afentanyl, sufentanil, rocuronium, vecuronium, atracurium, etc. The type of surgery may be surgery type coverage. The surgery type coverage refers to general surgery.

In this case, the anesthesia depth computing module 30 may automatically identify the drug type by means of the drug type identification unit 302. In other words, the drug type used by the anesthesia depth computing module 30 may be automatically identified according to the signal characteristic of the electroencephalogram signal and a preset prediction model comprising a correspondence relationship between signal characteristics of the electroencephalogram signal and a drug type.

In this embodiment, as shown in FIG. 2, the device 1 for processing an anesthesia electroencephalogram signal may further comprise a display module 40. The display module 40 may display the drug type and the anesthesia depth value. The display module 40 may be a screen or another display device.

FIG. 4 is a schematic diagram showing an interface of the display module 40 according to an embodiment. In some embodiment, as shown in FIG. 4, the interface of the display module 40 displays a drug target, a drug result, an anesthesia depth target, and an anesthesia depth value. There are three buttons [Confirm], [Edit] and [Cancel] in an operation area for the health care personnel or an operator to operate.

In this embodiment, the anesthesia depth model database includes an anesthesia depth model corresponding to each drug type. The target anesthesia depth model is selected according to the type of the anesthetic drug, and the anesthesia depth value is obtained based on the target anesthesia depth model and the collected electroencephalogram signal. In this case, there are differences between different drugs, and if the same anesthesia depth model is used, the resulting anesthesia depth value is not accurate enough. As a result, by using multiple drug models, the anesthesia depth can be obtained more accurately, and the adaptability to the type of the anesthetic drug is increased.

Figure 5:
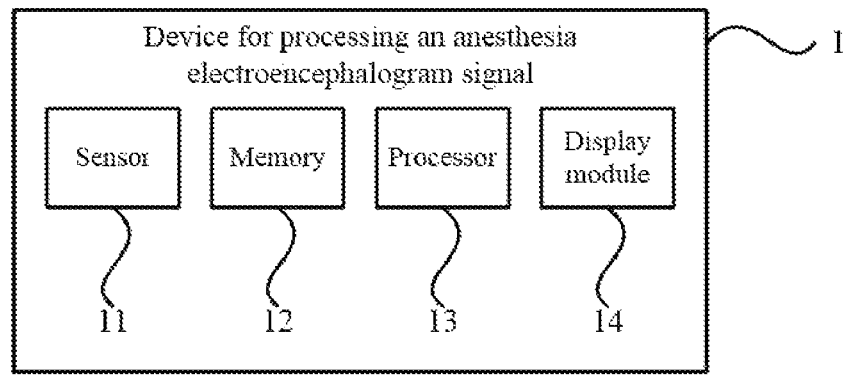
FIG. 5 is a schematic structural diagram showing a device for processing an anesthesia electroencephalogram signal according to an embodiment of the present disclosure.

The following is a device for processing an anesthesia electroencephalogram signal in some embodiment. FIG. 5 is a schematic structural diagram showing a device for processing an anesthesia electroencephalogram signal according to an embodiment.

In some embodiment, a device 1 for processing an anesthesia electroencephalogram signal is shown in FIG. 5. The device for processing an anesthesia electroencephalogram signal may comprise a sensor 11, a memory 12, a processor 13 and a display module 14.

In this embodiment, the sensor 11 may collect an electroencephalogram signal. In some embodiment, the sensor 11 may be electrode pads. In addition, the collection module 10 may also be other EEG collection apparatuses. The electroencephalogram signal acquired by the sensor 11 may be an analog electroencephalogram signal.

In this embodiment, the device 1 for processing an anesthesia electroencephalogram signal may further comprise an analog-to-digital (A/D) converter (not shown). The analog-to-digital (A/D) converter can convert the analog electroencephalogram signal into a digital electroencephalogram signal. As a result, this facilitates the storage of the electroencephalogram signal.

In this embodiment, the memory 12 may store the collected electroencephalogram signal. The memory may be RAM, FIFO, a memory bank, etc. In some embodiment, the memory is connected to the sensor 11, in which case, the electroencephalogram signal collected by the sensor 11 may be stored in the memory.

In this embodiment, the processor 13 can extract a signal characteristic of the electroencephalogram signal. The signal characteristic comprises one or more of a time-domain characteristic, a frequency-domain characteristic, and a non-linear-domain characteristic. The time-domain characteristic comprises an amplitude characteristic of the electroencephalogram signal, the frequency-domain characteristic comprises an electroencephalogram-related energy ratio, and the nonlinear-domain characteristic comprises an LZ complexity, a spectral entropy, a sample entropy, or an information entropy.

In this embodiment, the signal characteristic may be extracted per a time period. Of course, that is, the signal characteristic can be extracted periodically. The time period of extraction may be a fixed value. That is, the period of extraction remains unchanged. The time period of extraction may also be a variable value. That is, the period of extraction will change according to the actual situation.

In this embodiment, the processor 13 may also select a target anesthesia depth model from an anesthesia depth model database according to the determined drug type, the anesthesia depth model database being trained according to a specific, a corresponding electroencephalogram signal, and a marked anesthesia depth. An anesthesia depth value is obtained based on the target anesthesia depth model and the electroencephalogram signal.

In this embodiment, the anesthesia depth model database may comprise a plurality of anesthesia depth models. Each anesthetic drug corresponds to one of the anesthesia depth models. Each anesthesia depth model is trained with a corresponding specific anesthesia depth database. The specific anesthesia depth database includes a plurality of electroencephalogram signals throughout the anesthesia, anesthetic states corresponding to various segments of each of the electroencephalogram signals throughout the anesthesia, and a correspondence relationship between various segments of the electroencephalogram signal and anesthesia depths (that is, a correspondence relationship between signal characteristics of various segments of the electroencephalogram signal and anesthesia depths). Anesthetic states corresponding to various segments of the electroencephalogram signal comprise one or more of alertness, sedation, normal anesthesia, deep anesthesia, excessive deep anesthesia, and no electrical brain activity. As a result, the processor 13 may select a target anesthesia depth model from the anesthesia depth model database, and obtain an anesthesia depth value according to the signal characteristic of the collected electroencephalogram signal and the target anesthesia depth model. Here, the processor 13 is similar to the anesthesia depth computing module 30 described above.

In this embodiment, the drug type used by the processor 13 may be input by the user, or may be automatically identified according to the signal characteristic of the electroencephalogram signal and a preset prediction model comprising a correspondence relationship between at least one signal characteristics of an electroencephalogram signals and a drug type. However, this embodiment is not limited thereto, and the drug type used by the processor 13 may also be automatically identified, and confirmed by user input.

In this embodiment, the processor 13 may also determine the drug type according to the signal characteristic and a preset prediction model comprising a correspondence relationship between at least one signal characteristics of an electroencephalogram signal and a drug type.

In this embodiment, the preset prediction model is trained with a marked drug type database. The marked drug type database may comprise various types of drugs, electroencephalogram signals under the action of the various types of drugs, and corresponding signal characteristics of various segments of the electroencephalogram signals.

In this embodiment, the marked drug type database may further comprise a correspondence relationship between the types of drugs and the corresponding electroencephalogram signals (that is, the correspondence relationship between the drug type and the signal characteristics of the corresponding electroencephalogram signals). As a result, the trained prediction model may comprise the correspondence relationship between the drug type and the signal characteristics of the corresponding electroencephalogram signals. Therefore, the processor 13 may also determine the drug type according to the signal characteristic and the prediction model. Here, the processor 13 may refer to the relevant unit in the anesthesia depth computing module 30 that realize automatic identification.

In addition, in this embodiment, the processor 13 may also perform de-noising on the acquired electroencephalogram signal before performing the above-mentioned relevant processing on the collected electroencephalogram signal.

The de-noising process of the processor 13 can refer to the de-noising process in the de-noising module 20 described above. As a result, the processor 13 may also obtain the anesthesia depth value based on the target anesthesia depth model and the signal characteristic of the de-noised electroencephalogram signal. As a result, the anesthesia depth can be obtained more accurately.

In this embodiment, as shown in FIG. 5, the device 1 for processing an anesthesia electroencephalogram signal may further comprise a display module 14. The display module 14 is similar to the display module 40 described above.

Under normal circumstances, at different anesthetic states, the health care personnel may use only one type of anesthetic drug. In addition, at different anesthetic states, the health care personnel may use different types of anesthetic drugs. Therefore, the identification of the drug type is very necessary. Hereinafter, a method for identifying an anesthetic drug according to an embodiment will be described in detail with reference to FIG. 6.

Figure 6:
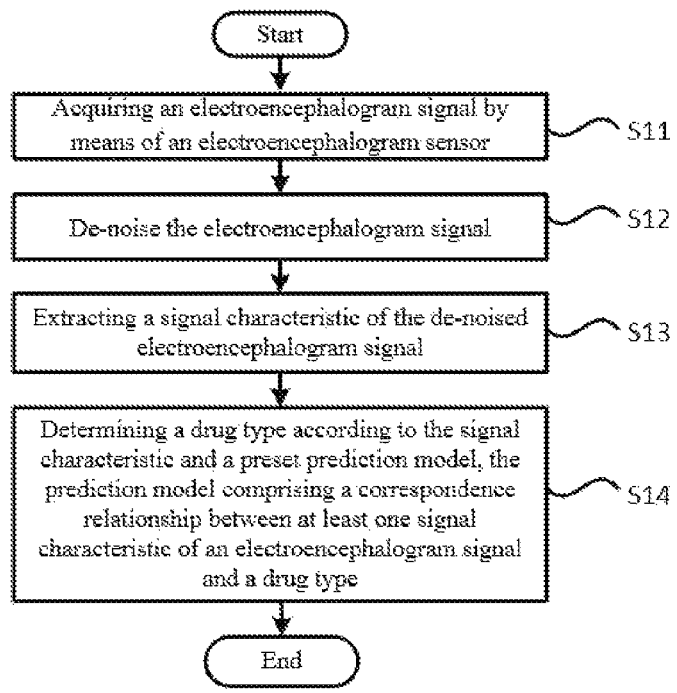
FIG. 6 is a schematic flowchart showing a processing method for identifying an anesthetic drug according to an embodiment of the present disclosure.

FIG. 6 is a schematic flowchart showing a method for identifying an anesthetic drug according to an embodiment of the present disclosure.

In this embodiment, as shown in FIG. 6, the method for identifying an anesthetic drug may comprise acquiring an electroencephalogram signal by means of an electroencephalogram sensor (step S11); de-noising the electroencephalogram signal (step S12); extracting a signal characteristic of the de-noised electroencephalogram signal (step S13); and determining the drug type according to the signal characteristic and a preset prediction model comprising a correspondence relationship between at least one signal characteristic of an electroencephalogram signal and a drug type (step S14).

In step S11, the electroencephalogram signal may be obtained by means of the electroencephalogram sensor. The electroencephalogram signal may also be collected by a single-channel, dual-channel or multi-channel EEG (electroencephalogram) apparatus. The collected electroencephalogram signal may comprise electroencephalogram signals of the patient at different anesthetic states.

In addition, in step S11, the collected electroencephalogram signal comprises interference signals, such as eye movement interference signals, and electromyogram interference signals. These interference signals affect the signal quality of the electroencephalogram signal.

In this embodiment, as shown in FIG. 6, the method for identifying an anesthetic drug may further comprise de-noising the electroencephalogram signal (step S12).

In step S12, the de-noising may comprise filtering low-frequency interference through high-pass filtering, filtering high-frequency interference through a low-pass filter, and detecting and removing interference signals such as electrooculograms and electromyograms.

In this embodiment, the electroencephalogram signal has a signal characteristic. As shown in FIG. 6, the method for identifying an anesthetic drug may further comprise extracting a signal characteristic of the de-noised electroencephalogram signal (step S13).

In this embodiment, the signal characteristic may be extracted per a time period. That is, the signal characteristic can be extracted periodically. The time period of extraction may be a fixed value. That is, the period of extraction remains unchanged. However, this embodiment is not limited thereto, and the time period of extraction may also be a variable value. That is, the period of extraction will change according to the actual situation.

In step S13, the signal characteristic comprises one or more of a time-domain characteristic, a frequency-domain characteristic, and a nonlinear-domain characteristic.

In this embodiment, a method for calculating the time-domain characteristic of the signal characteristic is as follows:

first, a movable window x(n) for one second is taken, where n=0, 1, 2 . . . N−1, and N refers to a sampling frequency. x(n) is an effective electroencephalogram signal. Then, the actual amplitude value AmpValue is solved according to formula (1):

$$AmpValue = \max_{0 \sim N-1} x(n) - \min_{0 \sim N-1} x(n) \quad (1)$$

Finally, the actual amplitude value AmpValue is compared with a prescribed amplitude threshold AmpThreshold. If AmpValue is greater than or equal to AmpThreshold, it is determined as "high amplitude"; and if AmpValue is less than AmpThreshold, it is determined as "low amplitude". The specified amplitude threshold AmpThreshold may be set according to the doctor's experience or actual requirements, for example, 50 μV.

In addition, in this embodiment, a method for calculating the frequency-domain characteristic of the signal characteristic is as follows:

in a first step, a movable window x(n) for one second is taken, where n=0, 1, 2 . . . N−1, and N refers to a sampling frequency. x(n) is an effective electroencephalogram signal. In a second step, FFT conversion is performed on x(n) according to formula (2), to acquire frequency-domain information X(k) of the electroencephalogram signal. The expression of formula (2) is as follows:

$$X(k) = DFT[x(n)] \quad (2)$$

In a third step, the EEG frequency domain is divided into 5 wave bands and 8 frequency ranges as shown in Table 1, and calculates the cumulative sum of the corresponding frequency ranges according to formulas (3)-(10).

$$\delta\_value = \Sigma_{0.5\,Hz}^{3\,Hz} X(k) \quad (3)$$

$$\theta\_value = \Sigma_{4\,Hz}^{7\,Hz} X(k) \quad (4)$$

$$\alpha1\_value = \Sigma_{8\,Hz}^{8.9\,Hz} X(k) \quad (5)$$

$$\alpha2\_value = \Sigma_{9\,Hz}^{10.9\,Hz} X(k) \quad (6)$$

$$\alpha3\_value = \Sigma_{11\,Hz}^{13\,Hz} X(k) \quad (7)$$

$$\beta1\_value = \Sigma_{14\,Hz}^{19.5\,Hz} X(k) \quad (8)$$

$$\beta2\_value = \Sigma_{20\,Hz}^{30\,Hz} X(k) \quad (9)$$

$$\gamma\_value = \Sigma_{31\,Hz}^{70\,Hz} X(k) \quad (10)$$

In a fourth step, the amounts δ_value, θ_value, α1_value, α2_value, α3_value, β1_value, β2_value, and γ_value obtained in the third step are sorted from the largest value to the smallest value. The largest value or a value floating within a certain range above and below the maximum value (for example, a floating range of 10%), the wave band in which these values are located is determined to be a "dominant wave band".

In addition, in this embodiment, a method for calculating the nonlinear-domain characteristic of the signal characteristic is as follows:

in a first step, a movable window x(n) for one second is taken, where n=0, 1, 2 . . . N−1, and N refers to a sampling frequency. x(n) is an effective electroencephalogram signal. In a second step, sequence coarse-graining is performed. Sequence coarse-graining comprises averaging and sequence conversion. The calculation of a mean value is as in formula (11), and the sequence conversion is as in formula (12). After the sequence coarse-graining process, S(n) is a character string sequence, such as S1S2 . . . Sn.

$$mean\_Value = \frac{\Sigma_0^{N-1} x(n)}{N} \quad (11)$$

$$S(n) = \begin{cases} 0, & x(n) < mean\_Vlaue \\ 1, & x(n) \geq mean\_Vlaue \end{cases} \quad (12)$$

In a fifth step, the complexity is calculated. Assuming that S and Q respectively represent two character strings, SQ represents the total character string spliced by S and Q, and SQπ represents a character string obtained by deleting the last character from SQ (π represents an operation for deleting the last character). Assuming that V(SQπ) represents the set of all different substrings of SQπ. The initializations of C(n), S, and Q are c(n)=1, S=S1, and Q=S2, so SQπ=S1.

Now assuming that S=S1S2 . . . Sr, and Q=Sr+1. If Q∈V(SQπ), it means that Sr+1 is a substring of S1S2 . . . Sr character string, then S remains unchanged, only Q is updated to Q=Sr+1Sr+2, and it is then determined whether Q belongs to V(SQπ) (at this time, since S is unchanged and Q is updated, SQπ should also be updated).

This is repeated until Q∈V(SQπ) is found. Provided that at this time, Q=Sr+1Sr+2 . . . Sr+i, which means that Sr+1 . . . Sr+i+1 is not a substring of S1S2 SrSr+1 . . . Sr+i+1. Therefore, C(n) is increased by 1. The Q is then combined into S, such that S is updated to S1S2 . . . SrSr+1 . . . Sr+i+1, to take Q as Q=S+r+i+1. The above steps are repeated until the last digit of Q is taken. In this way, S1S2 . . . Sn is decomposed into C(n) different substrings. The finally obtained C(n) is the complexity.

In this embodiment, the time-domain characteristic may comprise an amplitude characteristic of the electroencephalogram signal, the frequency-domain characteristic may comprise an electroencephalogram-related energy ratio, and the nonlinear-domain characteristic may comprise an LZ complexity, a spectral entropy, a sample entropy, or an information entropy.

In this embodiment, as shown in FIG. 6, the method for identifying an anesthetic drug may further comprise determining the drug type according to the signal characteristic and a preset prediction model comprising a correspondence relationship between at least one signal characteristic of an electroencephalogram signals and a drug type (step S14). As a result, the drug type can be automatically identified.

In step S14, the prediction model may be trained with the specific drug type and the corresponding electroencephalogram signals. A training model for the prediction model may be more than one of or any one of a random forest, a support vector machine, a deep neural network, and other training models. If the deep network is selected as the training model, the waveform can be directly analyzed without the need to extract the signal characteristic such as the time-domain, frequency-domain, or nonlinear-domain characteristic.

In some embodiment, in step S14, the random deep forest is selected as the training model for the prediction model. The prediction model may be trained with the drug database. The drug database may comprise specific types of drugs and corresponding electroencephalogram signals. The drug database may further comprise a correspondence relationship between the specific types of drugs and the corresponding electroencephalogram signals. Specifically, the drug database may further comprise a correspondence relationship between the types of drugs and the signal characteristics of the corresponding electroencephalogram signals.

In some embodiment, the correspondence relationship between the types of drugs and the signal characteristics of the corresponding electroencephalogram signals in the drug database may be the correspondence relationship between the time-domain characteristics and the frequency-domain characteristics in the signal characteristics of the electroencephalogram signals and the types of drugs.

In this embodiment, the electroencephalogram signals undergo a time-domain computing method to obtain two results, namely high amplitude and low amplitude. In addition, the electroencephalogram signals are divided into wave bands in the frequency domain, and the correspondence relationship between the wave bands and frequencies is as shown in Table 2 below. The electroencephalogram signals undergo a frequency-domain computing method to determine different dominant wave bands (for the time/frequency-domain computing method, see the characteristic extraction step for details). The correspondence relationship between the time-domain characteristics and frequency-domain characteristics and the types of drugs is as shown in Table 3 below.

TABLE 2

Wave band and frequency band division

| Wave band | Frequency range |
|---|---|
| δ wave | 0.5 to 3 Hz |
| θ wave | 4 to 7 Hz |
|  | 8 to 13 Hz |
| α wave | α1: 8 to 8.9 Hz |
|  | α2: 9 to 10.9 Hz |
|  | α3: 11 to 13 Hz |
| β wave | 14 to 30 Hz |
|  | β1: 14 to 19.5 Hz |
|  | β2: 20 to 30 Hz |
| γ wave | >31 Hz |

TABLE 3

Characteristic-drug type training set

| Characteristic | Drug type |
|---|---|
| Frequency-domain characteristic: δ wave and α3 wave dominate<br>Time-domain characteristic: High amplitude | Propofol |
| Frequency-domain characteristic: δ wave, θ wave, α1 wave and α2 wave dominate<br>Time-domain characteristic: High amplitude | Sevoflurane |
| Frequency-domain characteristic: δ wave, β2 and γ wave dominate<br>Time-domain characteristic: Low amplitude | Ketamine |
| Frequency-domain characteristic: δ wave dominates<br>Time-domain characteristic: Low amplitude | Dexmedetomidine |

In this embodiment, the prediction model is trained to obtain the correspondence relationship as shown in Table 2. In step S14, the drug type used may be determined according to the signal characteristic of the collected electroencephalogram signal and the prediction model. This embodiment is not limited thereto, and it is also possible to identify the types of drugs (for example, analgesic, and muscle relaxant drugs) other than the anesthetic drugs.

However, this embodiment is not limited thereto, and the signal characteristic in the correspondence relationship comprises at least one of a frequency-domain characteristic, a time-domain characteristic, and a nonlinear-domain characteristic of the electroencephalogram signal. For example, the signal characteristic may comprise a time-domain characteristic, a frequency-domain characteristic, and a nonlinear-domain, or comprise a frequency-domain characteristic and a nonlinear-domain. As a result, according to one or more of the signal characteristics and the prediction model, the drug type corresponding to the collected electroencephalogram signal can be obtained.

Figure 7:
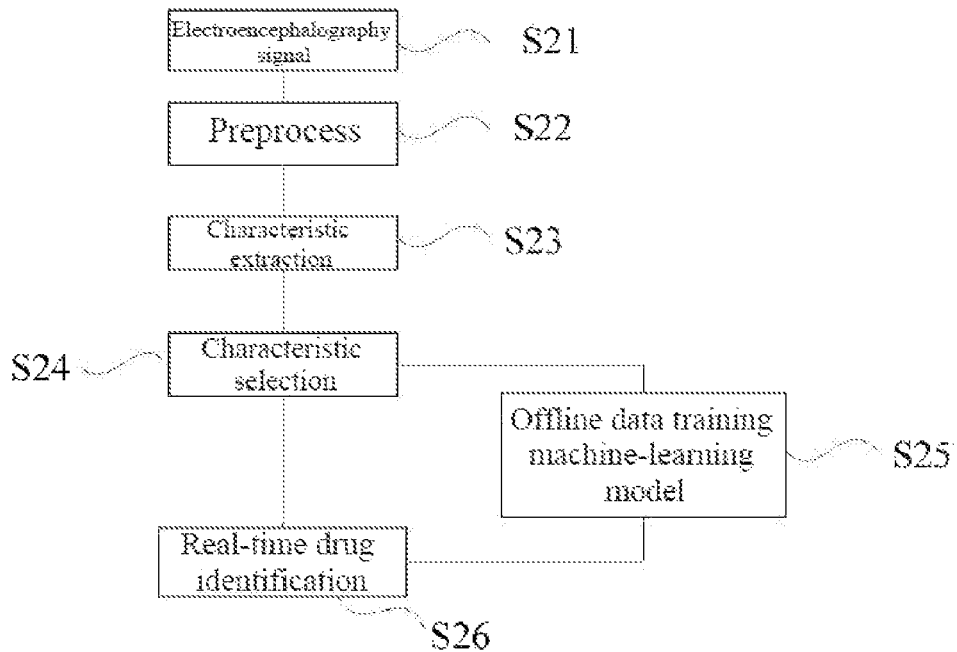
FIG. 7 is a schematic diagram showing a prediction model training process according to an embodiment of the present disclosure.

FIG. 7 is a schematic diagram showing a prediction model training process according to an embodiment.

In some embodiment, as shown in FIG. 7, the prediction model training process is as follows: an EEG signal under the action of a specific anesthetic drug is collected (step S21, this step can refer to step S11 described above). The high-quality electroencephalogram signal is obtained by means of preprocessing (that is, de-noising) (step S22, this step can refer to step S12 described above), and a signal characteristic is then calculated and extracted (step S23). The signal characteristic may be a time-domain or frequency-domain characteristic, or a nonlinear-domain characteristic, etc. (step S23 can refer to step S13 described above). However, this embodiment is not limited thereto, and it may also be an EEG signal and a corresponding signal characteristic under the action of a specific anesthetic drug that are stored in the drug type database. The calculated signal characteristic is selected (step S24). The selected signal characteristic may select one or more of time-domain, frequency-domain, and nonlinear-domain characteristics. Taking the signal characteristic as an input parameter and the drug type as an output parameter, an offline data operation processor is used to train a decision tree (step S25).

In addition, the real-time drug identification method based on FIG. 7 may further comprise outputting the drug type in real time (step S26). In the real-time drug identification method, step S21 is in a real-time state. Specifically, the EEG signals are collected in real time, and after the same preprocessing, and the characteristic calculation and extraction process, the calculated and selected characteristic is sent into the offline training decision tree for real-time analysis, and the drug type corresponding to the current waveform characteristic is analyzed and output.

In some embodiment, different types of drugs (anesthetic, analgesic, muscle relaxant drugs, etc.) may also be identified through joint analysis of electroencephalogram signals and other parameters (such as blood pressure, electromyograms, etc.).

In this embodiment, the method for identifying an anesthetic drug may further comprise outputting the drug type. That is, the drug type may be displayed by the display device. As a result, the drug type can be obtained intuitively.

Hereinafter, a method for processing an anesthesia electroencephalogram signal according to an embodiment will be described in detail with reference to FIG. 8.

Figure 8:
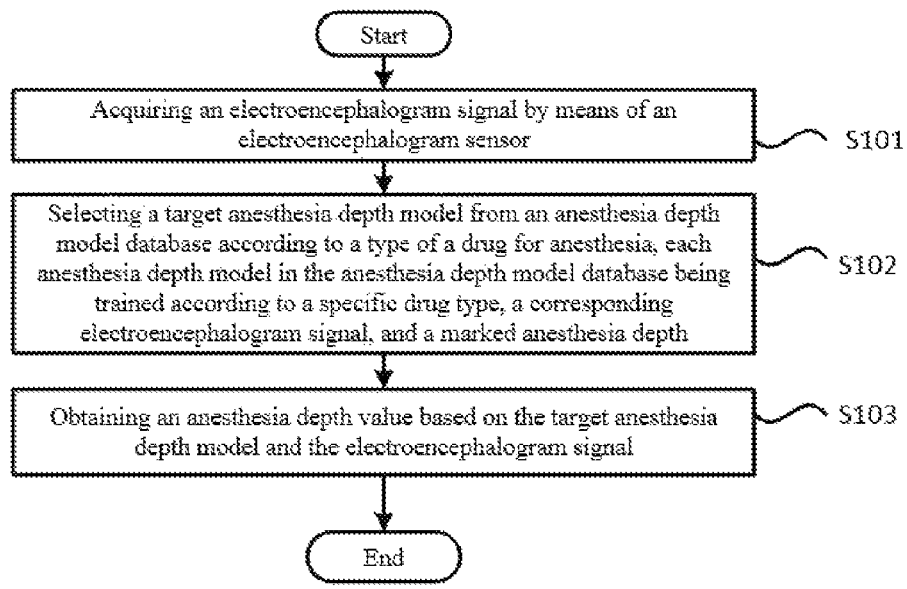
FIG. 8 is a schematic flowchart showing a method for processing an anesthesia electroencephalogram signal according to an embodiment of the present disclosure.

FIG. 8 is a schematic flowchart showing a method for processing an anesthesia electroencephalogram signal according to this embodiment.

In this embodiment, as shown in FIG. 8, the method for processing an anesthesia electroencephalogram signal may comprise acquiring an electroencephalogram signal by means of an electroencephalogram sensor (step S101). Here, step S101 is similar to step S11.

In step S101, the electroencephalogram signal may be collected by a sensor. For example, the collection of the electroencephalogram signal may be obtained by means of electrode pads (see step S11 described above). The electroencephalogram signal may also be collected by another EEG apparatus. The collected electroencephalogram signal may comprise electroencephalogram signals of the patient at different anesthetic states.

In this embodiment, the electroencephalogram signal comprises interference signals, which affect the signal quality of the electroencephalogram signal. In this case, the electroencephalogram signal may also be de-noised. The de-noising process is similar to the de-noising method in step S12.

In this embodiment, the de-noising may comprise filtering low-frequency interference through high-pass filtering, filtering high-frequency interference through low-pass filtering, and detecting and removing interference signals such as electrooculograms and electromyograms.

In this embodiment, the electroencephalogram signal generally has a signal characteristic. The signal characteristic may be one or more of a time-domain characteristic, a frequency-domain characteristic, and a nonlinear-domain characteristic. Characteristic extraction is performed on the electroencephalogram signal collected in step S101 or the de-noised electroencephalogram signal, and the extracted signal characteristic may be one or more of the time-domain characteristic, the frequency-domain characteristic, and the nonlinear-domain characteristic. When extracting the time-domain characteristic, the frequency-domain characteristic, and the nonlinear-domain characteristic, the calculation method used is similar to the method for calculating the signal characteristic involved in step S13.

In this embodiment, as shown in FIG. 8, the method for processing an anesthesia electroencephalogram signal may further comprise selecting a target anesthesia depth model from an anesthesia depth model database according to the type of a drug for anesthesia, the anesthesia depth model database being trained according to a specific drug type, a corresponding electroencephalogram signal, and a marked anesthesia depth (step S102), and obtaining an anesthesia depth value based on the target anesthesia depth model and the electroencephalogram signal (step S103). The target anesthesia depth model refers to an anesthesia depth model corresponding to the drug type used.

In step S102, the anesthesia depth model database may include an anesthesia depth model corresponding to each anesthetic drug. For example, for anesthetic drugs such as propofol, sevoflurane, ketamine and dexmedetomidine, these different types of anesthetic drugs act on the central nervous system, such that the produced electroencephalogram signals are different, and the corresponding anesthesia depths will also be different. In view of this, one drug corresponds to one anesthesia depth model, such that the anesthesia depth can be obtained more accurately, and the adaptability to the type of the anesthetic drug is increased.

In step S102, each anesthesia depth model is trained with a corresponding specific anesthesia depth database. The characteristic anesthesia depth database includes the drug type, electroencephalogram signals of people of different ages and from different populations under the specific drug, corresponding anesthesia depths recorded by doctors based on these electroencephalogram signals, and a correspondence relationship between various segments of the electroencephalogram signal and anesthesia depths (that is, a correspondence relationship between signal characteristics of various segments of the electroencephalogram signal and anesthesia depths). That is, the signal characteristic and the drug type are used as input parameters, and the anesthesia depth recorded by the doctor is used as an output parameter to train the anesthesia depth model. In this case, the anesthesia depth model database may be trained according to the specific drug type, a signal characteristic of the corresponding electroencephalogram signal, and a marked anesthesia depth. As a result, step S102 may also be obtaining the anesthesia depth value based on the target anesthesia depth model and the signal characteristic. Since the signal characteristic is one or more of the time-domain characteristic, the frequency-domain characteristic, and the non-linear-domain characteristic, the anesthesia depth corresponding to the electroencephalogram signal can be obtained from the characteristics of various aspects.

Figure 9:
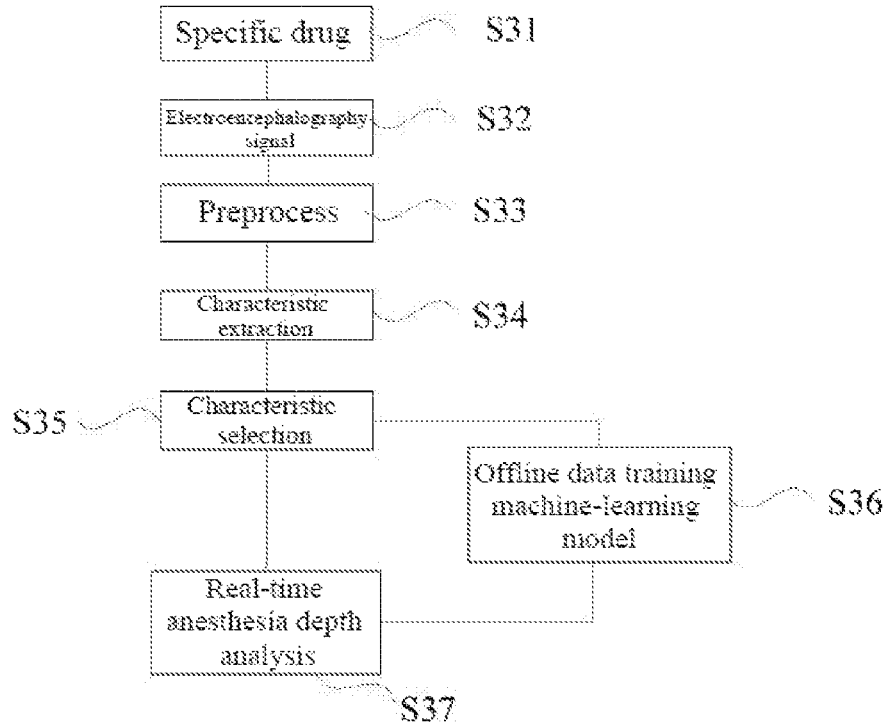
FIG. 9 is a schematic diagram showing an anesthesia depth model training process according to an embodiment of the present disclosure.

FIG. 9 is a schematic diagram showing an anesthesia depth model training process according to an embodiment.

In some embodiment, as shown in FIG. 9, the anesthesia depth model training process is as follows: a specific drug type is selected (step S31); an EEG signal under the action of a specific anesthetic drug is collected (step S32, this step can refer to step S11 described above); and the high-quality electroencephalogram signal is obtained after preprocessing (that is, de-noising) (step S33, this step can refer to step S12 described above), and a signal characteristic is then calculated and extracted (step S34). The signal characteristic may be a time-domain, frequency-domain, nonlinear-domain characteristic, etc. (step S34 can refer to step S13 described above). However, this embodiment is not limited thereto, and it may also be an EEG signal and a corresponding signal characteristic under the action of a specific anesthetic drug that are stored in the anesthesia depth model database. The calculated signal characteristic is selected (step S35). The selected signal characteristic may select one or more of time-domain, frequency-domain, and nonlinear-domain characteristics. Taking the signal characteristic and the drug type as input parameters and the anesthesia depth recorded by the doctor as an output parameter, an offline data operation processor is used to train an anesthesia depth model including more than 100 decision trees (step S36).

In addition, the method for processing a real-time anesthesia electroencephalogram signal based on FIG. 9 may further comprise outputting the anesthesia depth in real time (step S37). In the method for processing a real-time anesthesia electroencephalogram signal, step S32 is in a real-time state. Specifically, the EEG signals are collected in real time, and after the same preprocessing, and the characteristic calculation and extraction process, the calculated and selected characteristic is sent into the offline training anesthesia depth module for real-time analysis, and the anesthesia depth corresponding to the current waveform characteristic is analyzed and output.

In addition, in this embodiment, the training of the anesthesia depth model in step S102 and of the prediction model in step S16 may be performed by means of a random forest model. The steps of the random forest model are as follows:

in a first step, if the total number of training samples is N, a single decision tree randomly selects, with replacement, N1 training samples from the N training samples in a training set as training samples for this single tree. In a second step, if there are M input characteristics of the training sample, M1 input characteristics are randomly selected from the M input characteristics, where M1 is much smaller than M, and the best one is then selected from the M1 input characteristic cases for splitting. In a third step, each tree is split in this way until all the training samples at the node belong to the same class, and no pruning is needed. Multiple trees generated in a fourth step form a random forest, a random forest classifier is used to discriminate and classify the data, and the classification result is determined by the number of votes from the classifier.

In this embodiment, the drug type may be automatically identified according to the signal characteristic of the electroencephalogram signal and a preset prediction model comprising a correspondence relationship between signal characteristics of electroencephalogram signals and types of drugs.

In this embodiment, the drug type may be input by the user, or may be automatically identified according to the signal characteristic of the electroencephalogram signal and a preset prediction model comprising a correspondence relationship between signal characteristics of electroencephalogram signals and types of drugs, and confirmed by user input. The automatic identification can refer to the method for identifying an anesthetic drug described above.

In this embodiment, the electroencephalogram signal is further de-noised, such that step S103 may obtain the anesthesia depth based on the target anesthesia depth model and the de-noised electroencephalogram signal.

In addition, in this embodiment, the electroencephalogram signal has a corresponding signal characteristic. Step S103 may be obtaining the anesthesia depth value based on the target anesthesia depth model and the signal characteristic. As a result, the anesthesia depth can be obtained more accurately.

In addition, the method for processing an anesthesia electroencephalogram signal may further comprise displaying the anesthesia depth value (that is, outputting the anesthesia depth value). However, this embodiment is not limited thereto, and it is also possible to display the current type of the anesthetic drug, the drug target preset by the doctor, and the types of other drugs (e.g., analgesic, and muscle relaxant drugs). The method for processing an anesthesia electroencephalogram signal may also involve in presetting the drug type and the anesthesia depth level. As a result, the drug target (the drug type, and the anesthesia depth level) can be actually displayed and compared with the drug target preset by the doctor, to guide the medication, and to prevent type misuse and overdose. In this embodiment, each drug type has a corresponding anesthesia depth model, the target anesthesia depth model is selected according to the type of the anesthetic drug, and the anesthesia depth value is obtained based on the target anesthesia depth model and the electroencephalogram signal. In this case, the anesthesia depth can be obtained more accurately, and the adaptability to the type of the anesthetic drug is increased.

Figure 10:
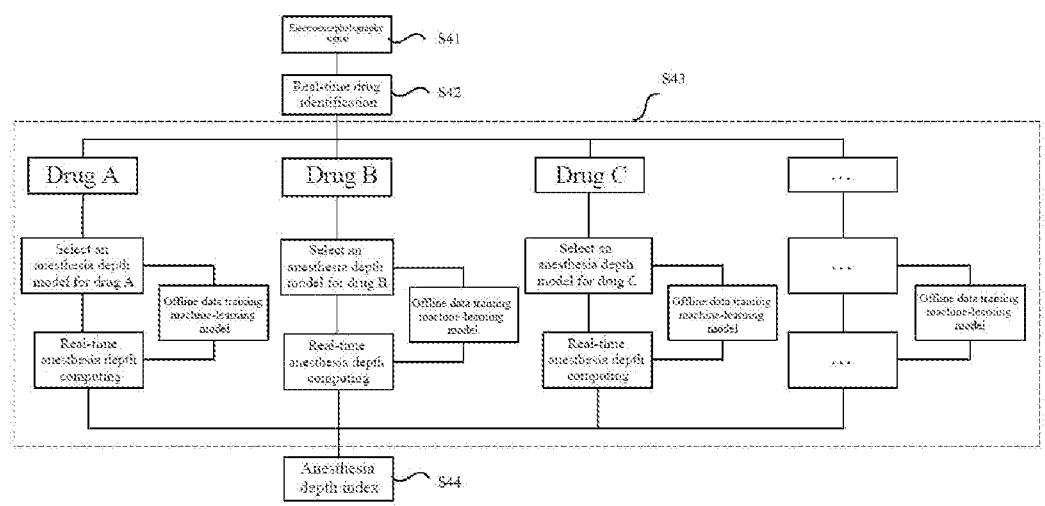
FIG. 10 is a schematic flowchart showing a method for processing an anesthesia electroencephalogram signal according to an embodiment of the present disclosure.

FIG. 10 is a schematic flowchart showing a method for processing an anesthesia electroencephalogram signal according to an embodiment.

In some embodiment, as shown in FIG. 10, a method for processing an anesthesia electroencephalogram signal is as follows: collecting an EEG signal in real time (step S41, this step can refer to step S11 described above), automatically identifying the drug type in real time according to the electroencephalogram signal (step S42, this step can refer to the method for identifying an anesthetic drug described above), and selecting a different model (step S43). The corresponding anesthesia depth model can be selected by comparing the identified drug type with the specific drug in each anesthesia depth model. Then, the signal characteristic (one or more of the time-domain, frequency-domain, and complexity) calculated in real time is used as an input parameter, the selected model is input for real-time analysis, and the anesthesia depth corresponding to the current waveform characteristic is analyzed and output (step S44).

In this embodiment, compared with the traditional method with a single model and parameter, the method for processing an anesthesia electroencephalogram signal can automatically identify different types of anesthetic drugs, and select the appropriate model and parameters according to different types of anesthetic drugs, thereby being adapted to different types of anesthetic drugs, and improving the accuracy of the anesthesia depth.

Figure 11:
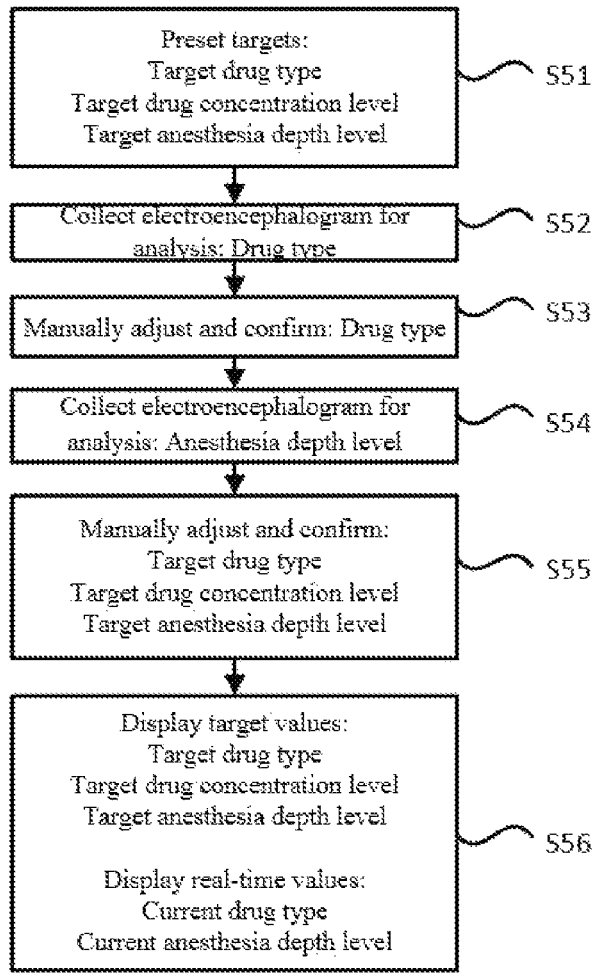
FIG. 11 is a schematic diagram showing the overall flow of a method for processing an anesthesia electroencephalogram signal according to an embodiment of the present disclosure.

FIG. 11 is a schematic diagram showing the overall flow of a method for processing an anesthesia electroencephalogram signal according to an embodiment.

In some embodiment, as shown in FIG. 11, the system operation process of a method for processing an anesthesia electroencephalogram signal is as follows:

a target is preset (step S51). The target may include the type of a drug, a drug concentration level, and an anesthesia depth level.

The drug type is automatically identified (step S52). The method for automatically identifying the drug type can refer to the above.

Health care personnel or an operator manually adjusts and confirms the displayed drug type (step S53).

A different anesthesia depth model is selected according to a different drug type to analyze and display the anesthesia depth level (step S54). The implementation of this step can refer to steps S102 and S103.

The health care personnel or the operator manually adjusts and confirms the achievement of the target (step S55). The adjusted and confirmed cases may comprise the drug type and the anesthesia depth level.

The adjusted or confirmed target value is displayed (step S56). That is, the automatically identified drug type, which has been manually adjusted or confirmed by the health care personnel or the operator, is displayed, and the real-time anesthesia depth level is displayed.

The method for processing an anesthesia electroencephalogram signal according to this embodiment can automatically distinguish different types of drugs while monitoring the anesthesia depth, so as to meet the requirements of monitoring the general anesthesia depth of different types of anesthetic drugs, and improve the accuracy.

Although the present disclosure is described above in detail with reference to the accompanying drawings and the embodiments. However, it may be understood that the foregoing description does not limit the present disclosure in any form. A person skilled in the art may make variations and changes to the present disclosure as required without departing from the essence, spirit, and scope of the present disclosure. All these variations and changes fall within the scope of the present disclosure.

What is claimed is:

1. A method for processing an anesthesia electroencephalogram signal, the method comprising:
   acquiring an electroencephalogram signal using an electroencephalogram sensor;
   extracting a signal characteristic of the acquired electroencephalogram signal;
   determining a drug type of an anesthetic drug that is currently applied to a patient according to the signal characteristic and a preset prediction model;
   selecting a target anesthesia depth model from an anesthesia depth model database according to the drug type of the anesthesia drug, each anesthesia depth model in the anesthesia depth model database being trained according to a specific drug type, an electroencephalogram signal corresponding to the specific drug type, a marked anesthesia depth, and a correspondence relationship between signal characteristics of the corresponding electroencephalogram signal and the marked anesthesia depths; and
   obtaining an anesthesia depth value based on the target anesthesia depth model and the acquired electroencephalogram signal, comprising: determining the anesthesia depth value according to signal characteristics of the acquired electroencephalogram signal and the correspondence relationship between the signal characteristics of the corresponding electroencephalogram signal and the marked anesthesia depths of the target anesthesia depth model,
   wherein the prediction model comprising a correspondence relationship between at least one signal characteristic of an electroencephalogram signal and a drug type, and determining the drug type of the anesthetic drug that is currently applied to the patient comprises:
   automatically identifying the drug type of the anesthetic drug according to the signal characteristic of the acquired electroencephalogram signal and the correspondence relationship between the at least one signal characteristic of an electroencephalogram signal and a drug type.

2. The method of claim 1, wherein before obtaining the anesthesia depth value based on the target anesthesia depth model and the electroencephalogram signal, the method further comprises:
   displaying the drug type.

3. The method of claim 2, wherein the drug type is anesthetic, and the method further comprises:
   displaying a doctor's preset drug target or types of non-narcotic drugs, the drug target comprising a drug type or a depth of anesthesia.

4. The method of claim 1, wherein after obtaining the anesthesia depth value, the method further comprises:
   outputting the anesthesia depth value.

5. The method of claim 1, wherein
   the signal characteristic is one of a time-domain characteristic, a frequency-domain characteristic, and a non-linear-domain characteristic.

6. The method of claim 1, wherein the anesthesia depth model database comprises multiple anesthesia depth models, and each anesthetic drug corresponds to one of the anesthesia depth models.

7. The method of claim 1, wherein the electroencephalogram signal corresponding to the specific drug type comprises various segments of the electroencephalogram signal throughout anesthesia, and anesthetic states corresponding to the various segments of the corresponding electroencephalogram signal comprise one or more of alertness, sedation, normal anesthesia, deep anesthesia, excessive deep anesthesia, and no electrical brain activity.

8. The method of claim 1, wherein the drug type is inputted by a user.

9. A method for processing an anesthesia electroencephalogram signal, the method comprising:
   acquiring an electroencephalogram signal using an electroencephalogram sensor;
   selecting a target anesthesia depth model from an anesthesia depth model database according to a drug type of an anesthesia drug, each anesthesia depth model in the anesthesia depth model database being trained according to a specific drug type, an electroencephalogram signal corresponding to the specific drug type, a marked anesthesia depth, and a correspondence relationship between signal characteristics of the corresponding electroencephalogram signal and the marked anesthesia depths; and
   obtaining an anesthesia depth value based on the target anesthesia depth model and the acquired electroencephalogram signal, comprising: determining the anesthesia depth value according to signal characteristics of the acquired electroencephalogram signal and the correspondence relationship between the signal characteristics of the corresponding electroencephalogram signal and the marked anesthesia depths of the target anesthesia depth model,
   wherein the drug type is automatically identified according to a signal characteristic of the electroencephalogram signal and a preset prediction model, and confirmed by a user input, the prediction model comprising a correspondence relationship between at least one signal characteristic of an electroencephalogram signal and a drug type.

10. The method of claim 9, wherein before obtaining the anesthesia depth value based on the target anesthesia depth model and the electroencephalogram signal, the method further comprises:
    displaying the drug type.

11. The method of claim 9, wherein the drug type is anesthetic, and the method further comprises:
    displaying a doctor's preset drug target or types of non-narcotic drugs, the drug target comprising a drug type or a depth of anesthesia.

12. The method of claim 9, wherein after obtaining the anesthesia depth value, the method further comprises:
    outputting the anesthesia depth value.

13. The method of claim 9, wherein
    the signal characteristic is one of a time-domain characteristic, a frequency-domain characteristic, and a non-linear-domain characteristic.

14. The method of claim 9, wherein the anesthesia depth model database comprises multiple anesthesia depth models, and each anesthetic drug corresponds to one of the anesthesia depth models.

15. The method of claim 9, wherein the electroencephalogram signal corresponding to the specific drug type comprises various segments of the electroencephalogram signal throughout anesthesia, and anesthetic states corresponding to the various segments of the corresponding electroencephalogram signal comprise one or more of alertness, sedation, normal anesthesia, deep anesthesia, excessive deep anesthesia, and no electrical brain activity.

* * * * *